(12) United States Patent
Dannenmaier et al.

(10) Patent No.: US 8,048,209 B2
(45) Date of Patent: Nov. 1, 2011

(54) DEGASSING DEVICE AND END-CAP ASSEMBLY FOR A FILTER INCLUDING SUCH A DEGASSING DEVICE

(75) Inventors: Jürgen Dannenmaier, Balingen (DE); Hermann Goehl, Bisingen (DE); Thomas Ertl, Bisingen (DE); Jacques Chevallet, Serezin du Rhône (FR); Francesco Ribolzi, Varese (IT)

(73) Assignee: Gambro Lundia AB, Lund (SE)

( * ) Notice: Subject to any disclaimer, the term of this patent is extended or adjusted under 35 U.S.C. 154(b) by 891 days.

(21) Appl. No.: 10/595,772

(22) PCT Filed: Nov. 2, 2004

(86) PCT No.: PCT/EP2004/012372
§ 371 (c)(1),
(2), (4) Date: Aug. 8, 2008

(87) PCT Pub. No.: WO2005/053772
PCT Pub. Date: Jun. 16, 2005

(65) Prior Publication Data
US 2009/0084720 A1    Apr. 2, 2009

(30) Foreign Application Priority Data
Nov. 24, 2003  (EP) .................................. 03026854
Nov. 24, 2003  (EP) .................................. 03026855

(51) Int. Cl.
*B01D 53/22* (2006.01)
*B01D 19/00* (2006.01)

(52) U.S. Cl. ............... 96/6; 96/8; 96/10; 96/11; 96/421; 95/46; 95/47; 95/51; 95/54; 55/510; 210/188; 210/321.6; 210/321.8; 210/321.89; 604/4.01; 604/6.09; 604/126

(58) Field of Classification Search .............. 96/4, 6, 96/8, 10, 11, 421; 95/46, 47, 51, 54; 55/510; 210/188, 321.6, 321.78, 321.8, 321.89; 604/4.01, 604/6.09, 126
See application file for complete search history.

(56) References Cited

U.S. PATENT DOCUMENTS
4,227,420 A    10/1980   Lamadrid
4,231,871 A *  11/1980   Lipps et al. ............... 210/321.8
(Continued)

FOREIGN PATENT DOCUMENTS
DE         4027531 C1     7/1991
(Continued)

OTHER PUBLICATIONS
WIPO, International Search Report, for PCT No. PCT/EP2004/012277, Published May 19, 2005, 3pgs.
(Continued)

*Primary Examiner* — Jason M Greene
(74) *Attorney, Agent, or Firm* — Nixon & Vanderhye P.C.

(57) ABSTRACT

A degassing device (203) comprises a first chamber (21) having an inlet for a liquid, and a second chamber (22) having an opening (23) closed by a hydrophobic membrane (24) and an outlet (25) for discharging the liquid. The first chamber (21) has a downstream portion that partially extends within the second chamber (22) and communicates therewith by a passageway (28). The second chamber (22) has a downstream portion that extends below the passageway (28) and asymmetrically surrounds the downstream portion of the first chamber (21).

39 Claims, 6 Drawing Sheets

U.S. PATENT DOCUMENTS

| | | | |
|---|---|---|---|
| 4,263,808 A | 4/1981 | Bellotti et al. | |
| 4,287,059 A | 9/1981 | Kume et al. | |
| 4,293,413 A * | 10/1981 | Schnell | 210/188 |
| 4,344,777 A | 8/1982 | Siposs | |
| 4,345,999 A | 8/1982 | Sigdell et al. | |
| 4,368,118 A | 1/1983 | Siposs | |
| 4,379,452 A | 4/1983 | DeVries | |
| 4,412,916 A | 11/1983 | Kell | |
| 4,433,971 A * | 2/1984 | Lindsay et al. | 604/122 |
| 4,436,620 A | 3/1984 | Bellotti et al. | |
| 4,479,760 A | 10/1984 | Bilstad et al. | |
| 4,479,761 A | 10/1984 | Bilstad et al. | |
| 4,479,762 A | 10/1984 | Bilstad et al. | |
| 4,493,693 A | 1/1985 | Bilstad et al. | |
| 4,568,366 A * | 2/1986 | Frederick et al. | 96/6 |
| 4,582,598 A | 4/1986 | Bilstad et al. | |
| 4,605,503 A | 8/1986 | Bilstad et al. | |
| 4,617,115 A | 10/1986 | Vantard | |
| 4,623,450 A | 11/1986 | Vantard et al. | |
| 4,662,906 A * | 5/1987 | Matkovich et al. | 96/6 |
| 4,666,598 A | 5/1987 | Heath et al. | |
| 4,676,467 A | 6/1987 | Palsulich | |
| 4,765,888 A | 8/1988 | Barthe et al. | |
| 4,784,768 A * | 11/1988 | Mathieu | 210/321.8 |
| 4,798,090 A | 1/1989 | Heath et al. | |
| 4,806,135 A | 2/1989 | Siposs | |
| 4,824,339 A | 4/1989 | Bainbridge et al. | |
| 4,919,802 A * | 4/1990 | Katsura | 210/188 |
| 5,200,090 A | 4/1993 | Ford et al. | |
| 5,441,636 A | 8/1995 | Chevallet et al. | |
| 5,468,388 A | 11/1995 | Goddard et al. | |
| 5,707,431 A | 1/1998 | Verkaart et al. | |
| 5,744,047 A | 4/1998 | Gsell et al. | |
| 5,849,065 A | 12/1998 | Wojke | |
| 6,176,903 B1 | 1/2001 | Wamsiedler | |
| 6,206,954 B1 | 3/2001 | Schnell et al. | |
| 6,315,815 B1 * | 11/2001 | Spadaccini et al. | 95/46 |
| 6,361,518 B1 | 3/2002 | Brierton et al. | |
| 6,582,386 B2 | 6/2003 | Min et al. | |
| D479,320 S | 9/2003 | O'Mahony et al. | |
| 7,238,224 B2 * | 7/2007 | Kent | 95/46 |
| 7,901,579 B2 * | 3/2011 | Brugger et al. | 210/645 |
| 2001/0052290 A1 * | 12/2001 | Nagai | 96/6 |
| 2003/0138349 A1 | 7/2003 | Robinson et al. | |

FOREIGN PATENT DOCUMENTS

| | | |
|---|---|---|
| EP | 0245782 A2 | 11/1987 |
| EP | 0 292 445 * | 11/1988 |
| EP | 0292445 A1 | 11/1988 |
| EP | 0591896 A2 | 4/1994 |
| FR | 2513884 | 4/1983 |
| WO | WO-00/25843 A1 | 5/2000 |

OTHER PUBLICATIONS

WIPO, International Search Report, for PCT No. PCT/EP2004/012528 Published May 19, 2005, 4pgs.

WIPO, International Search Report, for PCT No. PCT/EP2004/011707 Published May 19, 2005, 2pgs.

WIPO, International Search Report, for PCT No. PCT/EP2004/012372 Published Jun. 16, 2005, 3pgs.

EPO, European Search Report, Application No. 1529545, Published Jun. 1, 2005, 3pgs.

EPO, European Search Report, Application No. 1530995, Published May 18, 2005, 2pgs.

EPO, European Search Report, Application No. 1532994, Published May 25, 2005, 3pgs.

* cited by examiner

DEGASSING DEVICE AND END-CAP ASSEMBLY FOR A FILTER INCLUDING SUCH A DEGASSING DEVICE

The present invention relates to a degassing device and an end-cap assembly for a filter including such a degassing device.

A conventional filter for extracorporeal treatment of blood comprises a first and a second compartments separated by a membrane, the first compartment having an inlet and an outlet for the circulation of blood therethrough and the second compartment having an outlet for draining a liquid (e.g. plasma water, plasma, used dialysis liquid) and an inlet when the treatment (e.g. hemodialysis) requires the circulation of a treatment liquid (e.g. a dialysis liquid) in the second compartment. The membrane is enclosed in an elongated tubular housing closed at both ends by an end-cap comprising a nozzle used as an inlet/outlet port for the first compartment.

Such filters are used in various extracorporeal treatments of blood, such as hemodialysis, hemofiltration, hemodiafiltration, plasmapheresis. The same type of filter, usually referred to as hemodialyzer or hemofilter, is used for hemodialysis, hemofiltration, hemodiafiltration. The main difference between a hemodialyzer and a plasmafilter (i.e. a filter used in plasmapheresis) is the pore size of their respective membrane, a membrane for plasmapheresis allowing the proteins contained in blood to migrate therethough, whereas a membrane for hemodialysis does not.

In all these treatments, blood is withdrawn from the patient, flown through the first compartment of the filter, and returned to the patient. In hemodialysis, a dialysis liquid is simultaneously flown through the second compartment of the filter and the metabolic wastes (urea, creatinine) contained in blood migrate by diffusion through the membrane into the second compartment. In hemofiltration, a pressure difference is created across the membrane so that plasma water flows through the membrane into the second compartment of the filter. Here, metabolic wastes migrate by convection into the second compartment. In order to compensate for the loss of bodily fluid, the patient is simultaneously infused a sterile substitution solution. Hemodiafiltration is a combination of hemodialysis and hemofiltration, and, in this treatment, a dialysis liquid is flown through the second compartment and a substitution liquid is infused into the patient. In plasmapheresis, a pressure difference is created across the membrane so that plasma (i.e. plasma water and proteins) flows through the membrane into the second compartment of the filter. Once treated, the plasma is returned to the patient.

A machine for performing any of the above treatments comprises a peristaltic pump for withdrawing blood from a patient through a so-called "arterial" line connected at one end to the vascular circuit of the patient and at the other end to the inlet of the first compartment of a filter, for pumping blood into the filter, and for returning blood to the patient through a so-called "venous" line connected at one end to the outlet of the first compartment of the filter and at the other end to the vascular circuit of the patient. The treatment machine also usually comprises a first blood pressure sensor for measuring the pressure of blood in the arterial line upstream of the pump, a second blood pressure sensor for measuring the pressure of blood in the arterial line downstream of the pump, a third pressure sensor for measuring the pressure of blood in the venous line, a bubble detector for detecting air bubbles in the venous line and a clamp for closing the venous line, for example when air bubbles are detected by the bubble detector.

An arterial line typically comprises the following components connected together by segments of flexible tubes: a first Luer connector for connection to an arterial cannula, an arterial bubble trap, a pump hose for cooperating with the rotor of the peristaltic pump of the treatment machine, and a second Luer connector for connection to the inlet of the first compartment of the filter.

A venous line typically comprises the following components connected together by segments of flexible tubes: a first Luer connector for connection to the outlet of the first compartment of the filter, a venous bubble trap, and a second Luer connector for connection to a venous cannula. Usually, the first and third pressure sensors of the machine are connected to the arterial and venous bubble trap respectively, when the treatment machine, the arterial line, the venous line and the filter are assembled in view of a treatment.

A conventional bubble trap is basically an elongated container that, in use, is held vertically. The container has an inlet and an outlet for blood that are arranged so as not to be adjacent. It comprises also, in an upper location, a pressure measuring port for connection to a pressure sensor, an infusion port for infusing a liquid (e.g. a drug or a sterile saline solution) and an injection port for adding or removing air into or from the bubble trap so as to adjust the level of blood therein. In use, the bubble trap contains a volume of blood in a lower part that transiently stagnates therein so as to let gas bubbles and micro bubbles escape by gravity and join an upper part of the container full of air. In a conventional bubble trap, there is therefore always an interface blood-air.

Besides the fact that, in order to properly operate, conventional bubble traps must contain a certain volume of blood (which conflicts with the desirable minimization of the volume of blood outside of the body during extracorporeal blood treatments), their use is limited to relatively short treatment sessions because of the blood clotting resulting from long lasting blood-air interface. In this respect, they are adapted to chronic treatment (a treatment session for a chronic patient usually lasts about four hours), but they cannot be used for intensive care treatment (the treatment of an acute patient can last several days).

In addition, the assemblage of a bubble trap and the line connected thereto to a treatment machine and the setting of the blood level therein is relatively time consuming.

An object of the invention is to design a degassing device and an end-cap assembly including such a degassing device that remedy the above-mentioned limits of conventional extracorporeal blood circuit.

According to the invention, a degassing device comprises:
 a first chamber having an inlet for a liquid; and
 a second chamber having an opening closed by a hydrophobic membrane and an outlet for discharging the liquid,
wherein the first chamber has a downstream portion that partially extends within the second chamber and communicates therewith by a passageway, and the second chamber has a downstream portion that extends below the passageway and asymmetrically surrounds the downstream portion of the first chamber.

This degassing device presents several advantages.

First, it is very efficient and remains efficient over time. Also its allows for a compact design, i.e. a small internal volume. For example, It is possible to design such a degassing device with a total internal volume that is about half of the blood volume in conventional bubble traps.

Second, the degassing device operates without air-blood interface and it is therefore particularly adapted to long lasting treatments (e.g. continuous renal replacement therapies).

Third, it does not require any specific activity for its mounting on a treatment machine or for its setting in use (no adjustment of the level of the air-blood interface since there is no air-blood interface).

Additional or alternative features of the degassing device according to the invention are as follows:

- The downstream portion of the second chamber has a lateral wall that surrounds a longitudinal axis of the degassing device and a bottom wall that is inclined with respect to a longitudinal axis of the degassing device.
- The downstream portion of the first chamber has a lateral wall that is concentric to the lateral wall of the second chamber.
- The lateral wall of the downstream portion of the first chamber and the lateral wall of the downstream portion of the second chamber are substantially cylindrical.
- The downstream portion of the first chamber has a cross-section that is substantially the same as the cross-section of the passageway between the first and the second chamber.
- The downstream portion of the first chamber is substantially conical and the passageway between the first and the second chamber opens at the tip of the cone.
- The passageway between the first and the second chamber opens in the second chamber close to a wall delimiting an upstream portion of the second-chamber.
- The first chamber comprises an upstream portion having a decreasing cross section.
- The first chamber comprises an upstream portion having an increasing cross section.
- The second chamber comprises an upstream portion extending above the passageway that has a decreasing cross-section, with a larger cross-section that is substantially level with the passageway and a smaller cross-section that is substantially level with the hydrophobic membrane.
- The upstream portion of the second chamber is substantially frusto-conical.
- The outlet port opens in the downstream portion of the second chamber at a location furthest to the passageway.
- The ratio of the diameter of the passageway to the diameter of the second chamber at the level of the passageway is comprised between about 0.2 and about 0.5.
- The first chamber of the degassing device has a downstream portion having a cross-section selected with respect to a maximal flow rate of a liquid in a circuit connected to the degassing device so that the velocity of the liquid in the downstream portion of the first chamber is less than a predetermined velocity.
- The cross-section of the downstream portion of the first chamber is selected with respect to a maximal flow rate of a liquid of about 500 ml/min in a circuit connected to the degassing device so that the velocity of the liquid in the downstream portion of the first chamber is less than about 3 m/min.
- The cross-section of the second chamber of the degassing device at the level of the passageway is selected so that the ratio of the velocity of a liquid within a downstream portion of the first chamber to the velocity of the liquid within the second chamber at the level of the passageway is more than a determined value.
- The cross-section of the second chamber of the degassing device at the level of the passageway is selected so that the ratio of the velocity of the liquid within the downstream portion of the first chamber to the velocity of the liquid within the second chamber at the level of the passageway is at least about 2.
- The downstream portion of the second chamber forms an overflow for a fluid flowing from the first chamber into the second chamber.
- The first chamber, the second chamber and the passageway therebetween are arranged with respect to each other so that a flow pattern of a liquid flowing from the first chamber, through the second chamber and to the outlet port comprises a component that is tangential to the membrane.
- The flow pattern of a liquid flowing from the first chamber, through the second chamber and to the outlet port comprises an umbrella like component.
- The first chamber, the second chamber and the passageway therebetween are arranged with respect to each other so that a flow of liquid flowing from the first chamber, through the second chamber and to the outlet port keeps gas bubbles in motion along an inner surface of the hydrophobic membrane.
- The degassing device further comprises an inlet port for the infusion of liquid.
- The degassing device further comprises a pressure measurement port for connection to a pressure sensor.
- The degassing device further comprises a protective member for protecting the hydrophobic membrane against external blows and for limiting the deformation of the hydrophobic membrane when the pressure of the liquid within the degassing device exceeds a limit.
- The hydrophobic membrane is arranged in a plane substantially perpendicular to a longitudinal axis of the degassing device.

According to the invention, an end-cap assembly for a filtration device including a filtration membrane arranged in an elongated housing comprises:

- an end-cap having:
  - an end wall having a central axis,
  - a peripheral wall surrounding the end wall, for connection to an end of the housing, and
- a degassing device as defined above, connected to the end-cap so that the first chamber of the degassing chamber is in fluid communication with an interior of the en-cap.

Additional or alternative features of the end-cap assembly according to the invention are as follows:

- The degassing device has a longitudinal axis that coincides with the central axis of the end wall of the end-cap and the first chamber has a wall directly connected to the end wall of the end-cap.
- The end wall of the end-cap is substantially annular and the wall of the first chamber has circular cross section decreasing from a first end of larger section, by which the first chamber is connected to the end wall of the end cap, to a second end of smaller cross section forming the passageway between the first chamber and the second chamber.
- The degassing device has a longitudinal axis that is substantially parallel to and spaced apart from the central axis of the end wall of the end-cap, and the end cap assembly further comprises a lateral nozzle for connecting an interior of the end-cap to an inlet of the first chamber of the degassing device.
- The first chamber has a wall having circular cross section increasing from a first end of smaller section, which forms the inlet of the first chamber, to a second end of larger cross section, which forms the passageway between the first and the second chamber.

Another object of the invention is a filter including the end-cap assembly defined above.

Other features and advantages of the invention will appear on reading the detailed description that follows. Reference will be made to the appended drawings in which.

Figure 1:
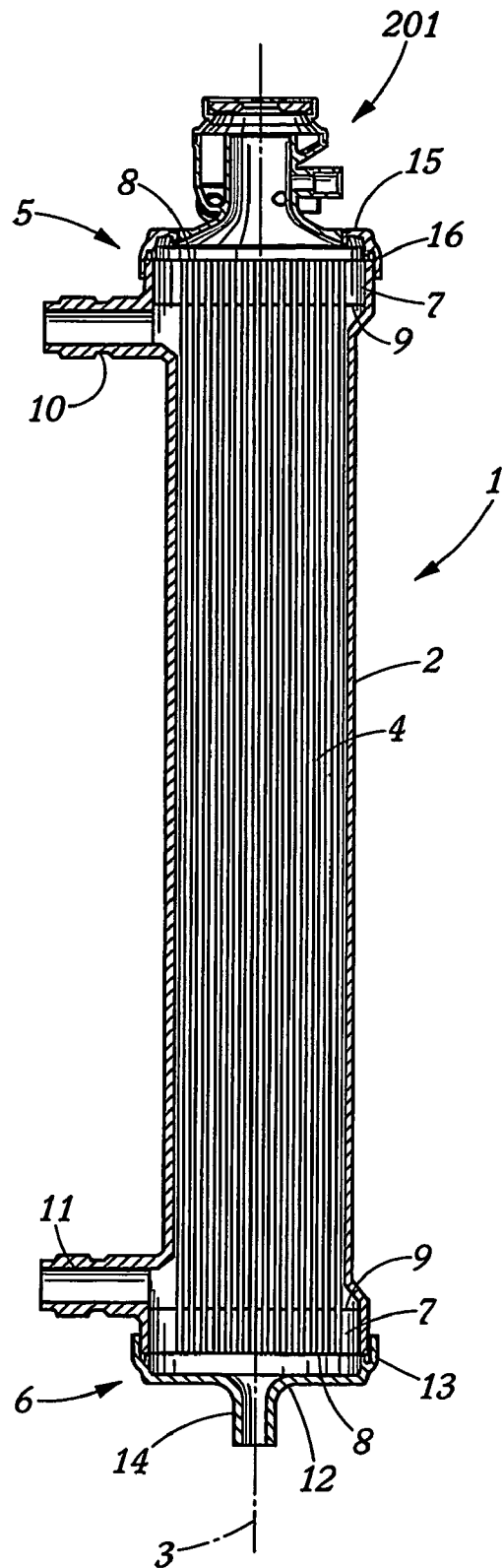
FIG. 1 is a cross-section view of a filter according to the invention, along a plane that contains the longitudinal axis of the filter.

FIG. 1 shows a hollow fiber filter 1 comprising a tubular housing 2 having a longitudinal axis 3, a semi-permeable membrane in the form a bundle of hollow fibers 4 extending within the housing 2 and secured thereto at both ends, and two end-caps 5, 6 closing the housing 2 at both ends. The ends of the fibers 4 are secured to the housing 2 by a potting compound in which they are embedded. The potting compound forms a disk 7 that extends perpendicularly to the longitudinal axis 3 of the housing 2. The ends of the fibers 4 open on an outer surface 8 of the disks 7 of potting material.

By construction, the hollow fiber filter 1 comprises a first and a second compartments separated from each other. The first compartment includes the interior of the hollow fibers 4 and the space delimited at each end of the filter between the outer surface 8 of the disk 7 of potting compound and the inner surface of the end-cap 5, 6, and the second compartment includes the space outside of the hollow fibers 4 that is delimited by the inner surface of the housing 2 and the inner surface 9 of the disks 7 of potting material. The housing 2 is fitted with two nozzles 10, 11 that give access to the second compartment.

In operation, the filter 1 is held substantially vertical, with the end-cap 6 in the lower position and the end cap 5 in the upper position.

The lower end-cap 6 comprises a circular end-wall 12 connected to a tubular peripheral wall 13 by which the end-cap 6 is secured to the housing 2. When the end-cap 6 is secured to the housing 2, as shown, the end-wall 12 is substantially perpendicular to the longitudinal axis 3 of the filter 1 and the tubular peripheral wall 13 is concentric to the housing 2. The end-cap 6 also comprises a tubular nozzle 14 connected to the end-wall 12 so that the central axis of the nozzle 14 coincides with the longitudinal axis 3 of the housing 2. The nozzle 14 forms the inlet of the first compartment.

The upper end-cap 5 comprises an annular end-wall 15 connected to a tubular peripheral wall 16 by which the end-cap 5 is secured to the housing 2. When the end-cap 5 is secured to the housing 2 of the filter 1, as shown, the longitudinal axis 3 of the filter 1 coincides with a central axis of the end wall 15, and the tubular peripheral wall 16 is concentric to the housing 2 of the filter 1.

Figure 2:
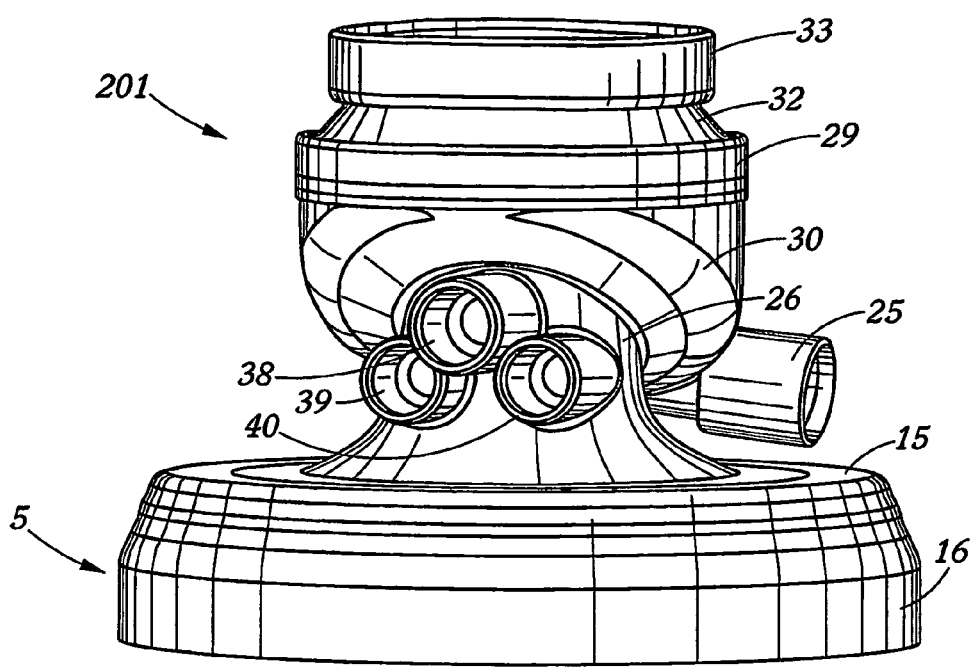
FIG. 2 is a perspective view of a first embodiment of an end-cap assembly according to the invention.
Figure 3:
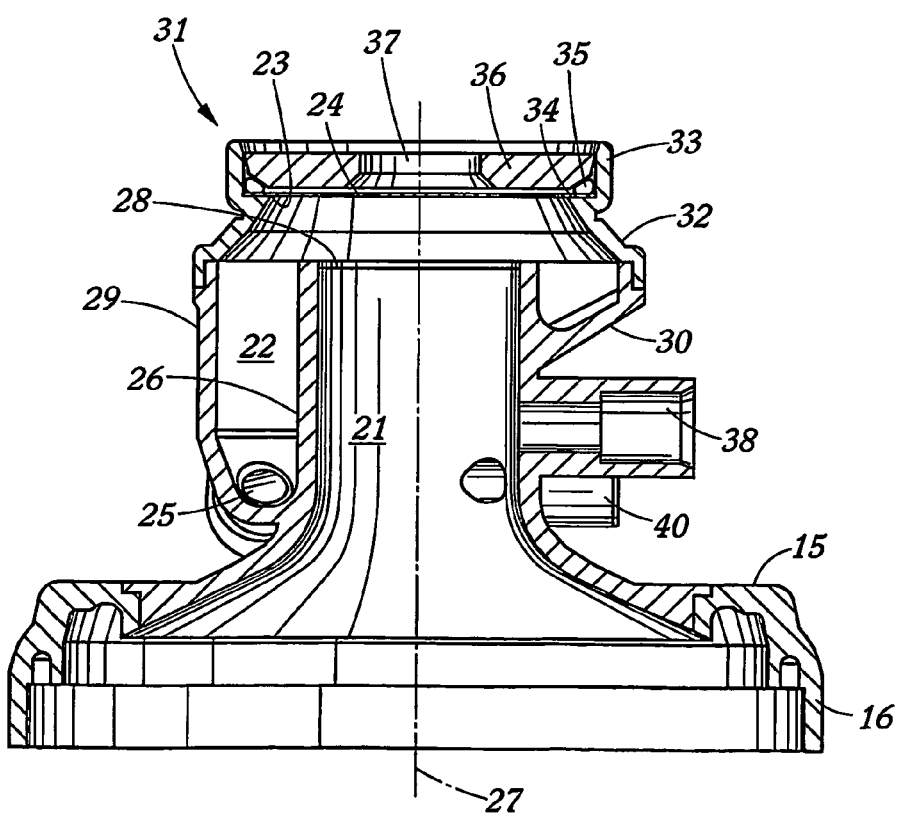
FIG. 3 is a cross-section view of the end-cap assembly of FIG. 2, along a plane that contains the central axis of the end-cap.

According to the invention, the end-cap 5 is connected to a degassing device 201 so as to form the end-cap assembly that is shown in details in FIGS. 2 and 3. The degassing device 201 has a longitudinal axis 27 that coincides with the longitudinal axis 3 of the filter 1, when the end-cap is secured to the housing 2 of the filter 1. The degassing device 201 comprises a first chamber 21 for receiving a liquid flowing out of the first compartment of the filter 1 into the end-cap 5; a second chamber 22 in communication with the first chamber 21 and having an opening 23 closed by a hydrophobic membrane 24; and an outlet port 25 connected to the second chamber 22 for discharging the liquid.

The first chamber 21 is delimited by a funnel like wall 26 having a first end of larger cross section, by which it is connected to the end-wall 15 of the end-cap 5, and a second end of smaller cross section, which defines a passageway 28 between the first chamber 21 and the second chamber 22. The funnel like wall 26 is centered on the longitudinal axis 27 of degassing device 201. In the direction of the flow, the first chamber 21 has therefore an upstream portion having a decreasing cross-section and a downstream portion having a constant cross-section (unless otherwise specified, "cross-section" means here and hereunder the transversal cross-section with respect to the longitudinal axis 27; also, the "direction of flow" means the direction of flow from the first compartment of the filter 2 to the outlet port 25 through the first and the second chambers 21, 22 of the degassing device 201).

The second chamber 22 has an upstream portion and a downstream portion that extend on each side of a plane containing the passageway 28 between the first and the second chambers 21, 22. The downstream portion is delimited by a cylindrical wall 29 that is concentric to the tubular portion of the funnel like wall 26, and by a bottom wall 30 that is beveled of about 45 degrees with respect the longitudinal axis 27. The highest point of the oblique bottom wall 30 is adjacent to the rim of the cylindrical wall 29. It results from the respective arrangement of the first chamber 21 and of the downstream portion of the second chamber 22 that the second chamber 22 forms an overflow for a liquid flowing from the first chamber 21 into the second chamber 22.

The outlet port 25 is comprised of a tubular wall that is connected to the cylindrical wall 29 of the second chamber 22, at the lowest point thereof. The central axis of the outlet port 25 is substantially perpendicular to the longitudinal axis 27 of the degassing device 201. The outlet port 25 extends tangentially to the cylindrical wall 29 of the second chamber 22.

It results from the shape of the second chamber 22 (cylindrical wall 29 connected to a slanting bottom wall 30), and from the connection of the outlet port 25 at the lowest point thereof, two characteristics that are of particular interest for a degassing device intended for blood: in comparison to a second chamber that would completely and symmetrically surround the first chamber or even only the upstream cylindrical portion of the first chamber, with a bottom wall substantially perpendicular to the longitudinal axis of the degassing device, the design represented in the figures allows for a degassing device having a minimal internal volume, and in which there is no area of relative stagnation for a liquid circulated through the degassing device. It was observed during the research work that led to the present invention, that with a second chamber completely surrounding the first chamber, with a bottom wall substantially perpendicular to the longitudinal axis of the degassing device, an area of relative stagnation appears in the second chamber opposite to the outlet port.

The upstream portion of the second chamber 22 is delimited by a lid 31 having a lower rim that is so dimensioned as to snugly engage an outer annular rabbet of the upper rim of the cylindrical wall 29. The lid 31 comprises a first, frusto-conical, wall 32 connected to a second, cylindrical, wall 33, the first wall 32 being connected to the second wall 33 by its smaller section. Note that the first wall 32 comprises in fact two frusto-conical portions, the lower portion having an angle that is slightly larger than the angle of the upper portion. The upstream portion of the second chamber 22 has therefore a decreasing cross-section. The lid 31 further comprises an inner annular shoulder 34 that extends at the junction between the frusto-conical wall 32 and the cylindrical wall 33. The aperture defined by the inner annular shoulder 34 forms the opening 23 of the second chamber 22 mentioned above. The annular shoulder 34 supports the hydrophobic membrane 24 at the periphery thereof. The membrane 24 is secured to the lid 31 by an O-ring 35 resting at the periphery of the membrane 24 and against which a disk-shaped stopper 36 is tightly engaged. The stopper 36, which snugly fits within the cylindrical wall 33 of the lid 31, comprises a vent 37 in its center through which the air removed from the liquid in the degassing device 30 can escape. Note that the membrane 24 does not abut on the inner surface of the stopper 36. The membrane 24 can therefore deform to a certain extent. When the positive pressure in the filter exceeds however a determined value, the membrane 24 abuts on the stopper 36 and does not run the risk of rupturing.

Three ports 38, 39, 40 are connected to the first chamber 21. The inlet ports 38, 39, 40 can be used for the infusion of various liquid (e.g. a substitution liquid or a drug, when the filter is a hemofilter) and for connection to a pressure sensor.

It results from the respective arrangement of the first chamber 21 and of the of the second chamber 22 that a liquid circulated through the degassing device 201 has an umbrella pattern with a longitudinal component within the first chamber 21 and a radial component within the upstream portion of the second chamber 22. The radial component of the flow tangentially sweeps the hydrophobic membrane 24 and helps prevent the formation of blood foam along its internal surface while keeping bubbles and micro bubbles in constant motion along the membrane until they escape therethrough.

Its is possible to optimize the efficiency of the degassing device of the invention by selecting the diameter of the downstream cylindrical part of the first chamber 21 (upper part of the wall 26) with respect to the maximal flow rate of blood within the extracorporeal blood circuit, as well as the size of the second chamber 22 (diameter of the cylindrical wall 29) with respect to the size of the first chamber 21 (diameter of the upper part of the wall 26) so that:

the maximal velocity of the liquid in the first chamber 21 (corresponding the maximal flow rate in the extracorporeal blood circuit) is never high enough to prevent the bubbles and micro-bubbles from migrating towards the hydrophobic membrane 24 and to expel them to the outlet port 25;

the velocity of the liquid entering the second chamber decreases to such an extent that bubbles and micro-bubbles can migrate by gravity towards the hydrophobic membrane 24.

For example, for a maximal blood flow rate of about 500 ml/min within the extracorporeal blood circuit, it was determined during the researches that led to the invention that an optimal velocity of blood within the downstream portion of the first chamber 21 (cylindrical part of wall 26) should be less than about 3 m/min and that the optimal ratio of the velocity of blood within the downstream portion of the first chamber 21 to the velocity of blood within the second chamber 22 at the level of the passageway 28 should be at least about 2.

A prototype of the degassing device 201 was made of molded polycarbonate: the diameter of the downstream portion of the first chamber 21 (cylindrical part of wall 26) was 16 mm; the inner diameter of the second chamber 22 at the level of the passageway 28 was 19 mm; the outer diameter of the second chamber 22 at the level of the passageway 28 was 32 mm; the diameter of the hydrophobic membrane 24 (useful surface) was 27 mm; the distance between the passageway 28 and the hydrophobic membrane 24 was 5 mm. The membrane was made of polytetrafluoroethylene and had a thickness of 0.13 mm and a pore size of 0.2 µm.

Bovine blood was circulated at a flow rate of 500 ml/mn in a closed loop circuit including a hemofilter connected to the prototype of degassing device 201. The velocity of blood within the degassing device was:

2.5 m/min in the downstream cylindrical portion of the first chamber 21;

2 m/min between the passageway 28 and the hydrophobic membrane 24;

1 m/min in the downstream portion of the second chamber 22, just below the level of the passageway 28; and 2 m/min in the downstream portion of the second chamber 14, just upstream of the outlet port 25.

The pressure in the degassing device was 50 mmHg. After four hours, 5 ml of air was injected in the circuit upstream of the hemofilter. After 15 minutes, the air injected in the circuit had been totally removed by the degassing device 201.

The end-cap 5, the walls 26, 29 and 30 that delimit the first chamber 21 and the downstream portion of the second chamber 22, and the ports 25 38, 39, 40 connected thereto, can be made by molding in one piece from a plastic material. A biologically inert material like polycarbonate is appropriate when the filter is for medical use. The lid 31 can also be made in one piece by molding, from the same material as the end-cap 5 and walls 26, 29, 30. The hydrophobic membrane 24 can be made of polytetrafluoroethylene.

The degassing device 201 is particularly adapted to remove gas from blood in an extracorporeal circuit of blood. The operation of the degassing device 201 in connection with, for example, the hemofilter 1, is as follows. Before a treatment session, the inlet of the first compartment (nozzle 14 of end-cap 6) of the hemofilter 1 is connected to an arterial blood line, and the outlet port 25 of the blood degassing device 201 is connected to a venous blood line. The hemofilter 1 is engaged in a holder keeping it substantially vertical, with the degassing device 201 being in the upper position. A bag of sterile saline solution is connected to the arterial line and the solution is pumped into the arterial line, the first compartment of the hemofilter 1, the degassing device 201 and the venous line, so as to rinse the extracorporeal blood circuit, to fill it with sterile saline solution and to remove air therefrom (preparatory steps called "priming" of the extracorporeal blood circuit). At the end of this process, there is no more air in the degassing device 201. Then, the arterial line is connected to a blood vessel of a patient, blood is pumped into the extracorporeal circuit while the saline solution flowing out of the venous line is collected in a waste bag. When blood reaches the end of the venous line, the venous line is in turn connected to the vessel of the patient and the treatment proper can start.

In the hemofilter 1, the blood flows within the hollow fibers 4, enters the end-cap 5, flows through the first chamber 21, pours into the second chamber 22 and leaves the degassing device 201 via the outlet port 25. Since the cross-section of the second chamber 22 at the level of the passageway 28 is substantially larger than the cross-section of the passageway 28 itself, the blood flow substantially decreases when blood enters the second chamber 22. This helps the bubbles and micro-bubbles that may be present in blood to move upwards by gravity towards the hydrophobic membrane 24. Also, because blood is directed by the funnel like wall 26 towards the hydrophobic membrane 24 and from then towards the frusto-conical wall 32 of the lid 31, the overall flow pattern of blood is umbrella like with a component that is tangential to the hydrophobic membrane 24. The membrane is therefore permanently swept and the creation of a layer of static blood foam on the inner surface of the membrane 24 is prevented. Instead, in particular thanks to the frusto-conical shape of the wall 32, the bubbles and micro-bubbles are kept in a permanent motion at the vicinity of the membrane 24, through which they pass shortly after entering the second chamber 22.

Figure 4:
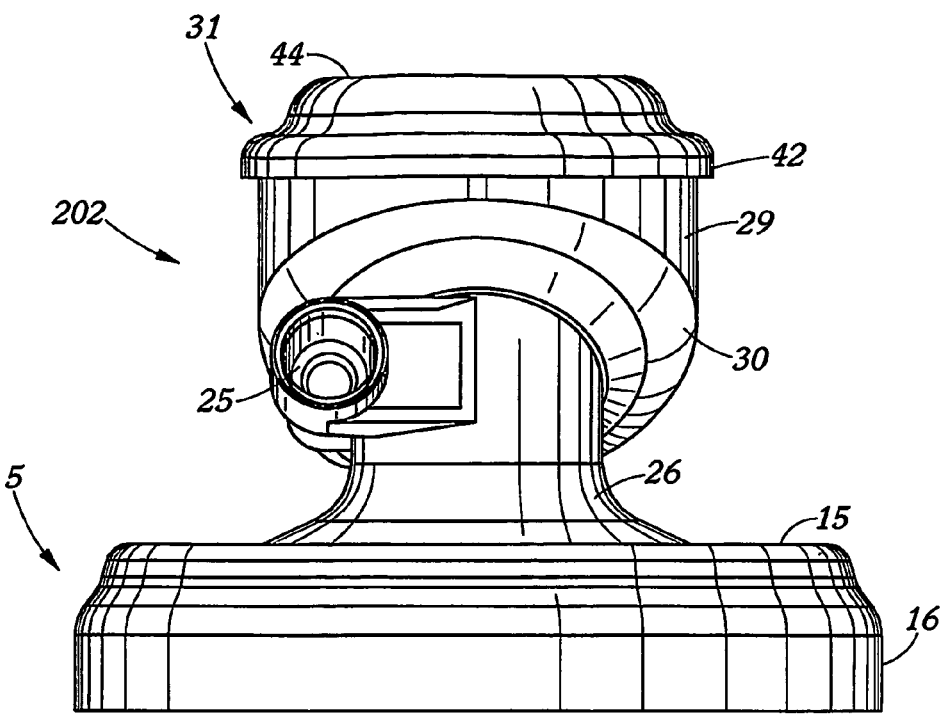
FIG. 4 is a front view of a second embodiment of an end-cap assembly according to the invention.
Figure 5:
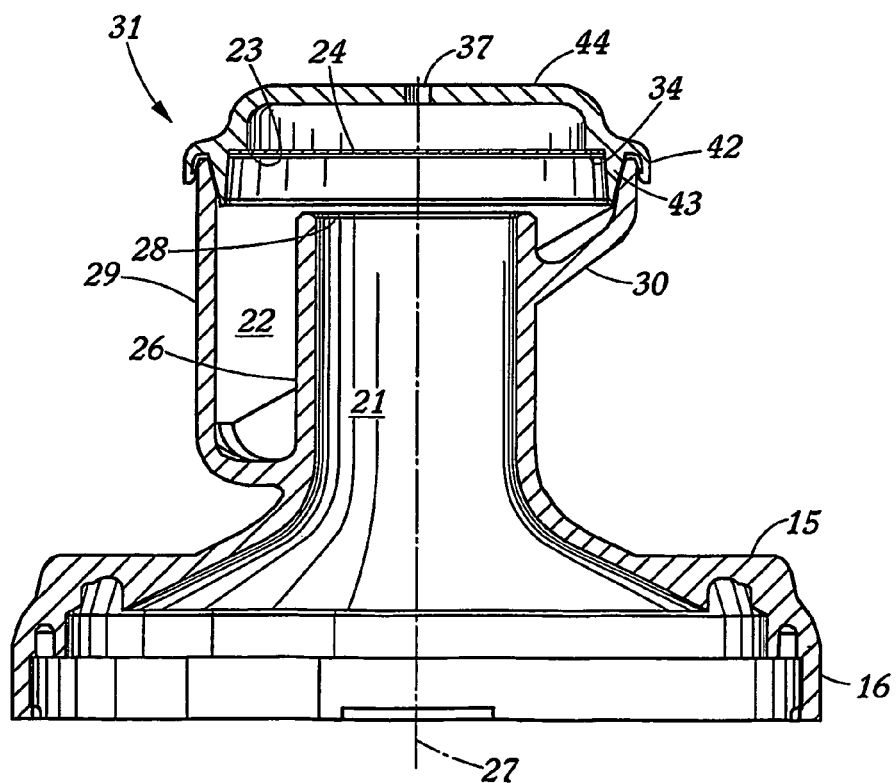
FIG. 5 is a cross-section view of the end-cap assembly of FIG. 4, along a plane that contains the central axis of the end-cap.

FIGS. 4 and 5 show a second embodiment of a degassing device 202 connected to an end-cap 5 according to the invention. The main differences between this second embodiment and the first embodiment of FIGS. 1 to 3 are as follows:

The outlet port 25 of the degassing device 202 is comprised of a tubular wall that is connected to the inclined wall 30 of the second chamber 22, at a lower point thereof. The central axis of the outlet port 25 is substantially perpendicular to the longitudinal axis 27 of the degassing device 202. The outlet port 25 extends inwardly, that is below the inclined wall 30 of the second chamber 22, tangentially to the upper cylindrical portion of the wall 26 of the first chamber 21.

The degassing device 202 is not fitted with any additional port (for the infusion of various liquid or for connection to a pressure sensor).

The upstream portion of the second chamber 22 is defined within a capsule like lid 31 fitting on the upper rim of the cylindrical wall 29 of the second chamber 22. More specifically, the upstream portion of the second chamber 22 is delimited by an inner peripheral wall 43 of the lid 31, which has a slightly frusto-conical inner surface, and by a circular hydrophobic membrane 24 closing an opening 23 of the second chamber 22 within the lid 31 defined by an inner annular shoulder 34. The hydrophobic membrane 24 is secured (e.g. by gluing) at its periphery to the shoulder 34 and is perpendicular to the longitudinal axis 27 of the degassing device. In more details, the capsule like lid 31 comprises a circular flat top wall 44 connected to the inner peripheral wall 43 and to an outer peripheral wall 42. The inner peripheral wall 43 and the outer peripheral wall 42 define therebetween a groove corresponding to the upper rim of the cylindrical wall 29 of the second chamber 22, so that the lid 31 can be engaged into the rim of the cylindrical wall 29 and secured thereto, e.g. by gluing. The lid 31 also comprises a vent 37 in the middle of the circular flat top wall 44. The annular shoulder 34 is spaced apart from the top wall 44 of the lid 31 so that the hydrophobic membrane 24 can deform under positive pressure. The top wall 44 of the lid 31 essentially protects the hydrophobic membrane 24 against outside blows.

Figure 6:
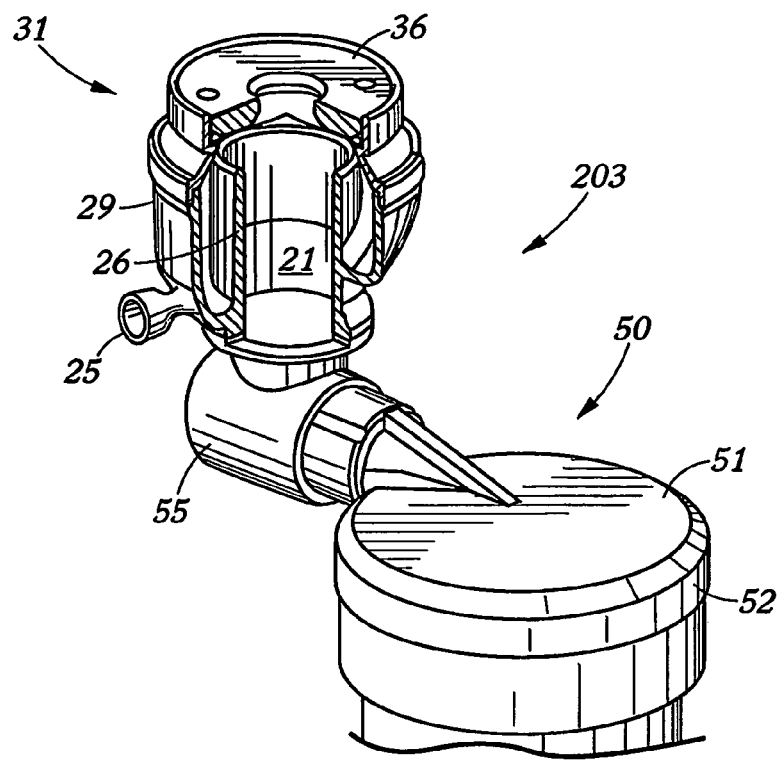
FIG. 6 is a perspective view, partially cut-away, of a third embodiment of the end-cap assembly according to the invention.
Figure 7:
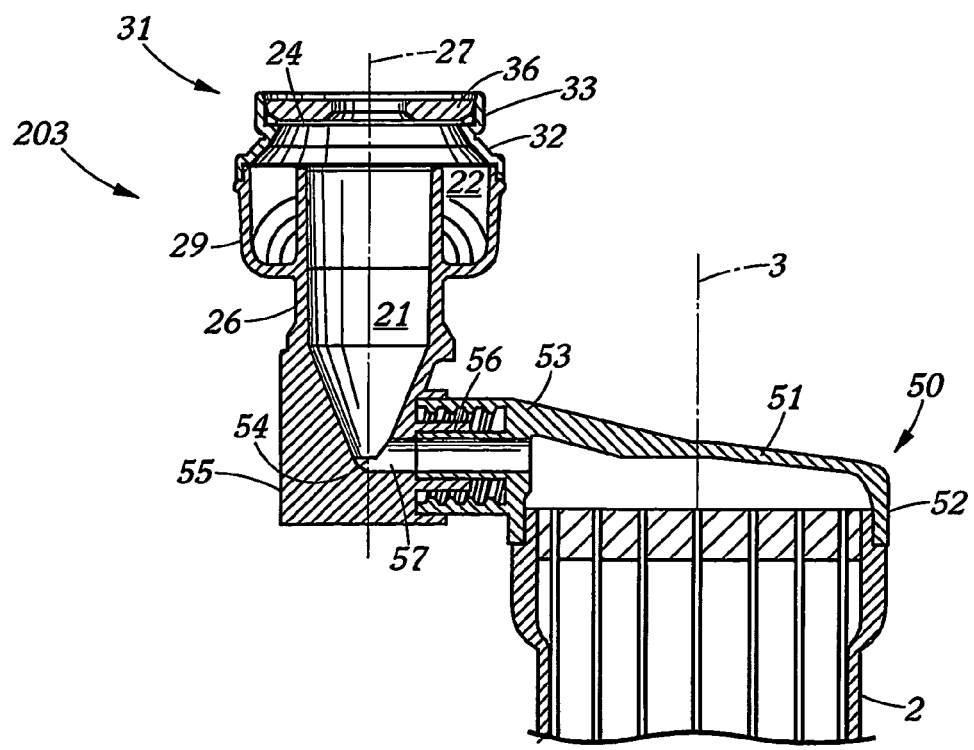
FIG. 7 is a cross-section view of the end-cap assembly of FIG. 6, along a plane that contains the central axis of the end-cap.

FIGS. 6 and 7 show a third embodiment of the invention. The main difference between this third embodiment and the first embodiment of FIGS. 1 to 3 resides in the connection of the degassing device 203 to the end cap 50. In the embodiment of FIGS. 1 to 3, the degassing device 201 is connected on the top of the end-cap 5 so that the longitudinal axis 27 of the degassing device 201 coincides with the central axis of the end cap 5. In the embodiments of FIGS. 6 and 7, the degassing device 203 is laterally connected to the end-cap 50 so that the longitudinal axis 27 of the degassing device 203 is parallel to and offset with respect to the central axis 3 of the end cap 50.

In more details, the end-cap 50 comprises a circular end-wall 51 connected to a tubular peripheral wall 52 by which the end-cap 50 is secured to the housing 2 of a filter. The end-cap 50 further comprises a nozzle 53 that radially extends from the circular end wall 51 so that the longitudinal axis of the nozzle 53 is perpendicular to the central axis of the end-cap 5. The nozzle 53 is fitted with a female Luer connector.

The degassing device 203 is very similar to the degassing device 201 shown in FIGS. 1 to 3, save for two characteristics:

The central axis of the outlet port 25 intersects and is substantially perpendicular to the longitudinal axis 27 of the degassing device 203.

The first chamber 21 comprises a conical upstream portion connected by its larger section to the downstream cylindrical portion. The inlet 54 of the first chamber 21 opens at the tip of the conical upstream portion. Also, the degassing device 203 comprises a coupling base 55 fitted with a male Luer connector 56 complementary to the female Luer connector of the nozzle 53 of the end-cap 50. The connecting base 55 includes a channel 57 that connects the inlet 54 of the first chamber 21 to the bore of the male Luer connector 56. The longitudinal axis of the channel 57 and of the bore of male Luer connector 56 coincide and are perpendicular to the longitudinal axis 27 of the degassing device 203.

Figure 8:
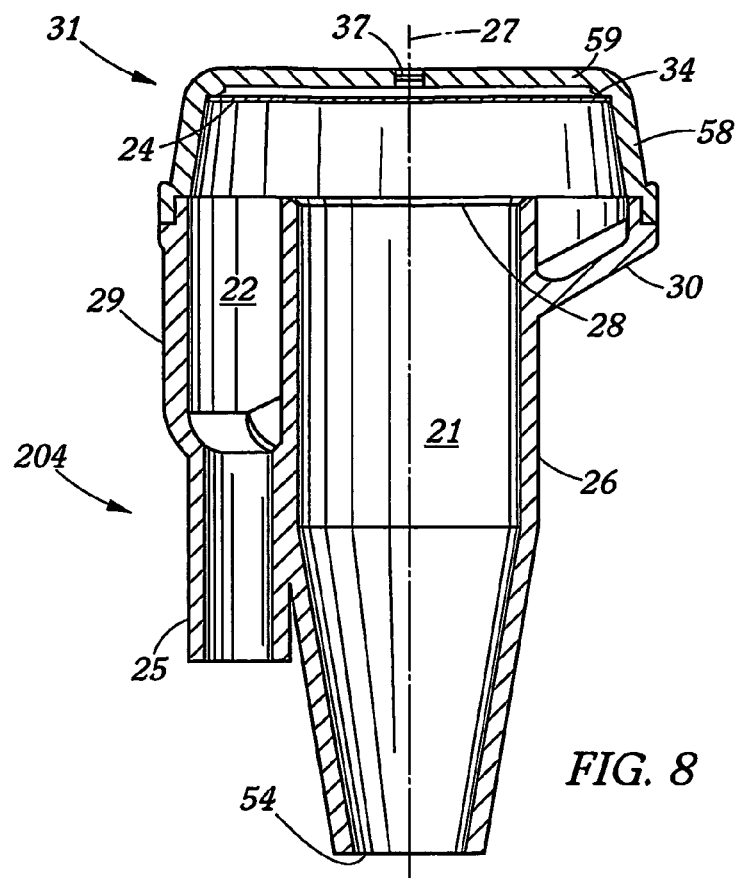
FIG. 8 is a cross-section view of a degassing device according to the invention, along a plane that contains the central axis of the end-cap.
Figure 9:
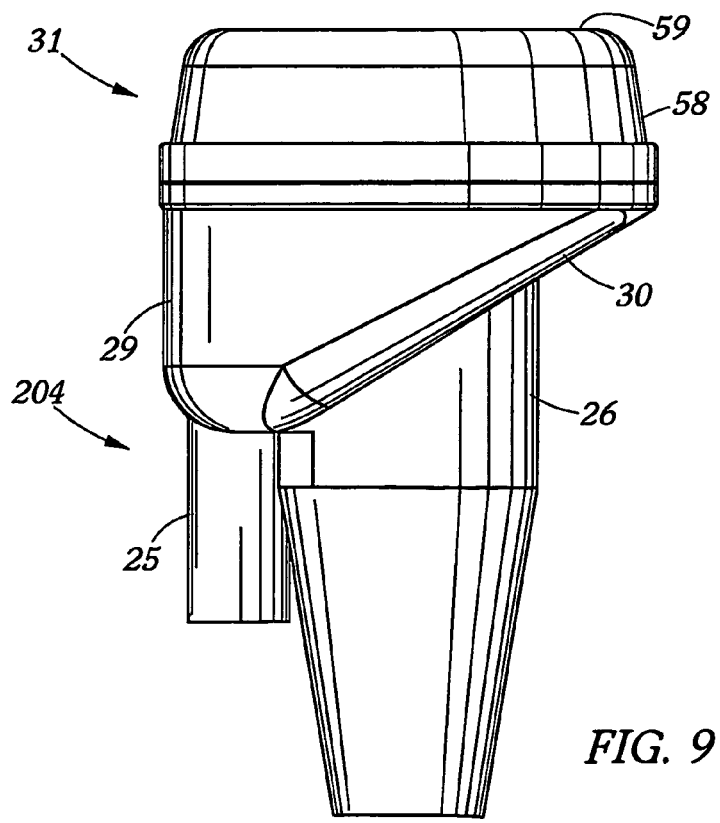
FIG. 9 is a front view of the degassing device of FIG. 8.

FIGS. 8 and 9 show another embodiment of degassing device according to the invention. The main differences between this degassing device and the degassing device of FIGS. 4 and 5 are as follows:

The wall of the upstream portion of the first chamber 21 of the degassing device 204 is frusto-conical and connects by its larger section to the downstream cylindrical wall 26.

The outlet port 25 of the degassing device 204 is comprised of a tubular wall that is connected to the inclined wall 30 of the second chamber 22, at a lower point thereof. The central axis of the outlet port 25 is substantially parallel to the longitudinal axis 27 of the degassing device 205. The outlet port 25 extends downwardly, that is below the inclined wall 30 of the second chamber 22, tangentially to the upper cylindrical portion of the wall 26 of the first chamber 21.

The lower rim of the frusto-conical wall 58 of the lid 31 comprises an annular inner rabbet. The upper rim of the cylindrical wall 29 of the second chamber 22 comprises a corresponding outer annular rabbet so that the lid 31 can engage the cylindrical wall 29 and form therewith a tight joint. The rims of the lid 31 and of the cylindrical wall 29 are dimensioned so that when the lid 31 is engaged on the top of the circular wall 29 the inner surfaces thereof are flush.

The inner annular shoulder 34 to which the hydrophobic membrane 24 is secured within the lid 31 is close to the top wall 59 of the lid 31. The hydrophobic membrane 24 can deform under positive pressure until it abuts against the top wall 59 of the lid 31. The lid 31 therefore protects the hydrophobic membrane 24 not only against outside blows but also from high positive pressure.

Figure 10:
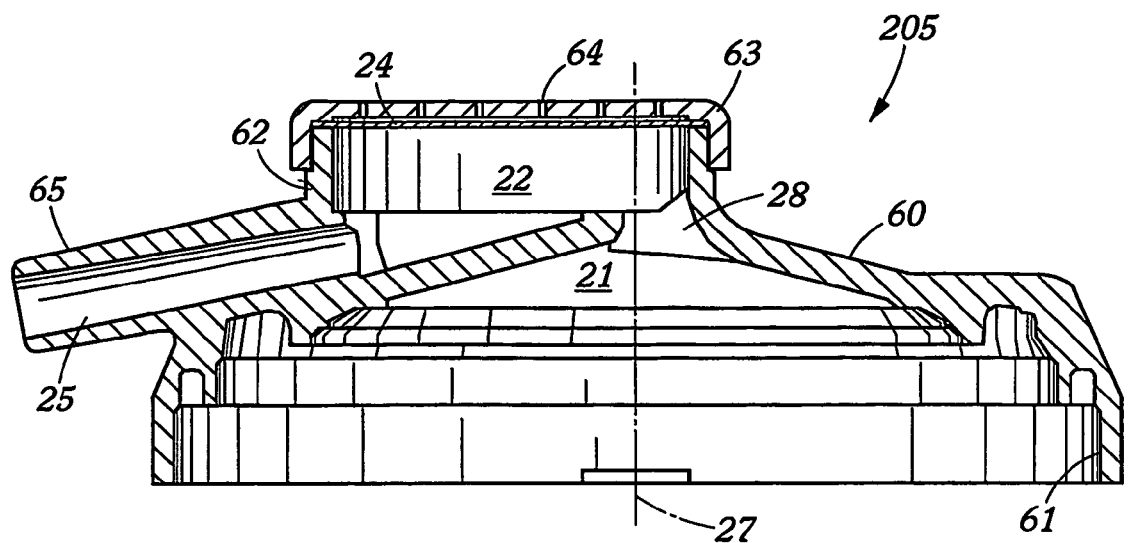
FIG. 10 is cross-section view of a fourth embodiment of the end-cap assembly according to the invention, along a plane that contains the central axis of the end-cap.

FIG. 10 shows a fourth embodiment of an end-cap assembly according to the invention. The end-cap assembly comprises a convex, conical end-wall 60 connected to a tubular peripheral wall 61 by which the end-cap assembly can be secured to the housing of a filter. The conical end-wall 60 delimits the first chamber 21 of a degassing device 205, which has therefore a decreasing section in the direction of flow. The conical end-wall 60 comprises an aperture at the tip thereof that forms a passageway 28 between the first chamber 21 and a second chamber 22. The second chamber 22 is delimited by a cylindrical wall 62 connected to the conical wall 60, and by the corresponding portion of the conical wall 60, which forms the bottom of the second chamber 22. The central axis of the cylindrical wall 62 is parallel to and offset with respect to the central axis 27 of the conical end-wall 60 (and of the degassing device) and the passageway 28 opens in the second chamber 22 adjacent to the cylindrical wall 62. A circular hydrophobic membrane 24 is secured to the upper rim of the cylindrical wall 62 so as to close the second chamber 22. A capsule like lid 63 having a series of vents 64 is engaged on the cylindrical wall 62 over the hydrophobic membrane 24 so as to protect the membrane 24 from outside and to support it and limit its deformation when it is subjected to a positive pressure from inside the filter. An outlet nozzle 65 forming the outlet port 25 of the degassing device 205 is connected to the cylindrical wall 62 opposite to the passageway 26.

The operation of the degassing device of FIG. 10, when connected to an extracorporeal blood circuit, is as follows. Since the cross-section of the second chamber 22 at the level of the passageway 28 is substantially larger than the cross-section of the passageway 28 itself, the blood flow substantially decreases when blood enters the second chamber 22. This helps the bubbles and micro-bubbles that may be present in blood to move upwards by gravity towards the hydrophobic membrane 24. Also, because blood is directed towards the hydrophobic membrane 24 at the periphery of the second chamber 22, the flow of blood has a component that is tangential to the hydrophobic membrane 24. The membrane is therefore permanently swept and the creation of a static layer of blood foam on the inner surface of the membrane 24 is prevented. Instead, the bubbles and micro-bubbles are kept in a permanent motion at the vicinity of the membrane 24, through which they pass shortly after entering the second chamber 22.

Figure 11:
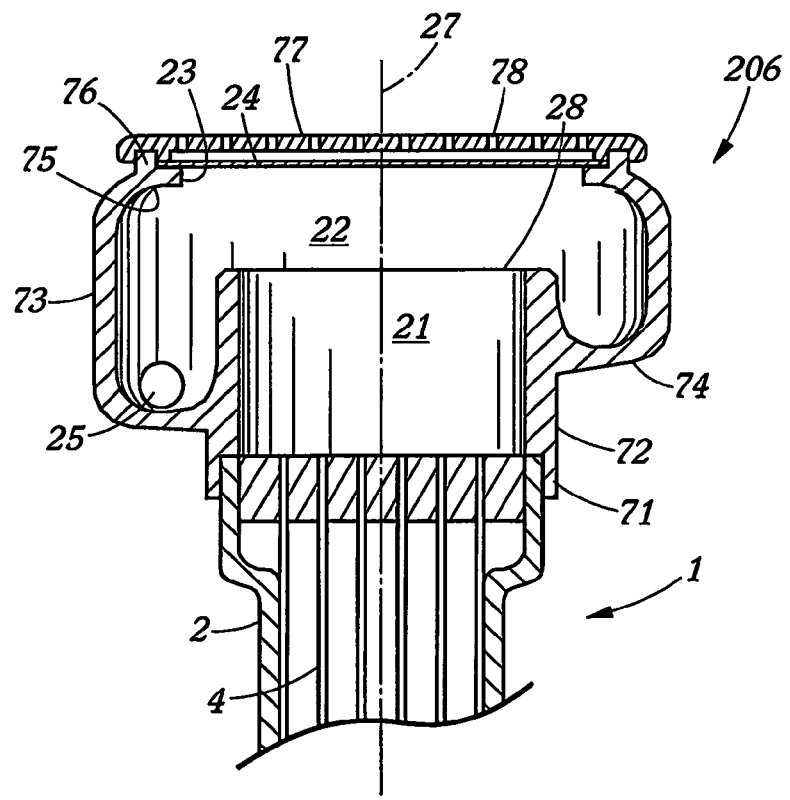
FIG. 11 is cross-section view of a fifth embodiment of the end-cap assembly according to the invention, along a plane that contains the central axis of the end-cap.

FIG. 11 shows a fifth embodiment of the end-cap assembly according to the invention. In this embodiment, the end-cap consists of a cylindrical peripheral wall 71 that engages the end of the housing 2 of a filter 1.

The cylindrical peripheral wall 71 forms the lower part of a cylindrical wall 72 that delimits the first chamber 21 of a degassing device 206. The first chamber 21 has a constant circular cross-section and its diameter is the same as the inner diameter of the end of the housing 2. The first chamber 21, which is centered on the longitudinal axis 27 of the degassing device 206, opens within a second chamber 22. The second chamber 22 is delimited by a cylindrical wall 73 concentric to the cylindrical wall 72 of the first chamber 21, and a bottom wall 74 that is beveled with respect to the longitudinal axis 27 of the degassing device 206. The passageway 28 between the two chambers 21, 22 has the same cross-section as the end of the housing 2 of the filter 1 and a liquid flown into the first chamber of the filter 1 passes therefore unimpeded from the hollow fibers 4 into the second chamber 22. The cross-section of the second chamber 22 at the level of the passageway 28 is larger than the cross-section of the passageway 28 and the second chamber 22 therefore forms an overflow for the first chamber 21. The upper part of the wall 73 that delimits the second chamber 22 is curved towards the longitudinal axis 27 of the degassing device 206 and defines an upper part of the second chamber 22 having a decreasing cross-section. The end of the wall 73 forks into two perpendicular circular rims 75, 76. A first rim 75 extends in a plane perpendicular to the longitudinal axis 27 so as to form an annular shoulder defining an opening 23 of the second chamber 22. This opening 23 is closed by a hydrophobic membrane 24 secured at its periphery to the annular shoulder. A second rim 76 extends parallely to the longitudinal axis 27. A capsule like lid 77 having a series of vents 78 is engaged onto the second rim 76 so as to protect the membrane 24 from outside and to support it and limit its deformation when it is subjected to a positive pressure from inside the filter. The degassing device 206 comprises an outlet port 25 connected to the second chamber 22.

The various embodiments of the invention described above are only to exemplify the invention. The scope of the invention is therefore not limited to any of them.

The invention claimed is:

1. A degassing device, comprising:
   a first chamber having an inlet for a liquid; and
   a second chamber having:
      an opening closed by a hydrophobic membrane;
      a liquid inlet port for the infusion of the liquid, and
      an outlet for discharging the liquid,
   wherein the first chamber has a downstream portion that partially extends within the second chamber and communicates therewith by a passageway, and the second chamber has a downstream portion that extends below the passageway and asymmetrically surrounds the downstream portion of the first chamber and
   wherein the downstream portion of the second chamber has a first lateral wall surrounding a longitudinal axis of the degassing device and a bottom wall inclined with respect to the longitudinal axis.

2. A degassing device according to claim 1, wherein the lateral wall is a first lateral wall, and the downstream portion of the first chamber has a second lateral wall that is concentric to the first lateral wall of the second chamber.

3. A degassing device according to claim 2, wherein the second lateral wall of the downstream portion of the first chamber and the first lateral wall of the downstream portion of the second chamber are substantially cylindrical.

4. A degassing device according to claim 1, wherein the downstream portion of the first chamber has a cross-section that is substantially the same as a cross-section of the passageway between the first and the second chamber.

5. A degassing device according to claim 1, wherein the downstream portion of the first chamber is substantially conical and the passageway between the first and the second chamber opens at a top of the substantially conical downstream portion, and along a direction of flow.

6. A degassing device according to claim 5, wherein the passageway between the first and the second chamber opens along the direction of flow to the second chamber close to a wall delimiting an upstream portion of the second chamber.

7. A degassing device according to claim 1, wherein the first chamber comprises an upstream portion having a decreasing cross section.

8. A degassing device according to claim 1, wherein the first chamber comprises an upstream portion having an increasing cross section.

9. A degassing device according claim 1, wherein the second chamber comprises an upstream portion extending above the passageway that has a decreasing cross-section, with a larger cross-section that is substantially level with the passageway and a smaller cross-section that is substantially level with the hydrophobic membrane.

10. A degassing device according to claim 9, wherein the upstream portion of the second chamber is substantially frusto-conical.

11. A degassing device according to claim 1, wherein the outlet port opens in the downstream portion of the second chamber at a location furthest to the passageway.

12. A degassing device according to claim 1, wherein a ratio of a diameter of the passageway to a diameter of the second chamber at the level of the passageway is comprised between about 0.2 and about 0.5.

13. A degassing device according to claim 1, wherein the first chamber of the degassing device has a downstream portion having a cross-section selected with respect to a maximal flow rate of a liquid in a circuit connected to the degassing device so that a velocity of the liquid in the downstream portion of the first chamber is less than a predetermined velocity.

14. A degassing device according to claim 13, wherein the cross-section of the downstream portion of the first chamber is selected with respect to a maximal flow rate of a liquid of about 500 mL/min in a circuit connected to the degassing device so that the velocity of the liquid in the downstream portion of the first chamber is less than about 3 ml/min.

15. A degassing device according to claim 1, wherein a cross-section of the second chamber of the degassing device at the level of the passageway is selected so that a ratio of a velocity of a liquid within a downstream portion of the first chamber to a velocity of the liquid within the second chamber at the level of the passageway is more than a determined value.

16. A degassing device according to claim 15, wherein the cross-section of the second chamber of the degassing device at the level of the passageway is selected so that the ratio of the velocity of the liquid within the downstream portion of the first chamber to the velocity of the liquid within the second chamber at the level of the passageway is at least about 2.

17. A degassing device according to claim 1, wherein the downstream portion of the second chamber forms an overflow for a fluid flowing from the first chamber into the second chamber.

18. A degassing device according to claim 1, wherein the first chamber, the second chamber and the passageway therebetween are arranged with respect to each other so that a flow pattern of a liquid flowing from the first chamber, through the second chamber and to the outlet comprises a component that is tangential to the membrane.

19. A degassing device according to claim 18, wherein the flow pattern of the liquid flowing from the first chamber, through the second chamber and to the outlet comprises an umbrella-like component.

20. A degassing device according to claim 1, wherein the first chamber, the second chamber and the passageway therebetween are arranged with respect to each other so that a flow of liquid flowing from the first chamber, through the second chamber and to the outlet keeps gas bubbles in motion along an inner surface of the hydrophobic membrane.

21. A degassing device according to claim 1, further comprising:
a pressure measurement port for connection to a pressure sensor.

22. A degassing device according to claim 1, further comprising:
a protective member for protecting the hydrophobic membrane against external blows and for limiting a deformation of the hydrophobic membrane when a pressure of the liquid within the degassing device exceeds a limit.

23. A degassing device according to claim 1, wherein the hydrophobic membrane is arranged in a plane substantially perpendicular to a longitudinal axis of the degassing device.

24. An end-cap assembly for a filtration device including a filtration membrane arranged in an elongated housing, the end-cap assembly, comprising:
an end-cap having:
an end wall having a central axis, and
a peripheral wall surrounding the end wall for connection to an end of the housing, and
a degassing device according to claim 1 connected to the end-cap so that the first chamber of the degassing chamber is in fluid communication with an interior of the end-cap.

25. An end-cap assembly according to claim 24, wherein the degassing device has a longitudinal axis that coincides with the central axis of the end wall of the end-cap and the first chamber has a wall directly connected to the end wall of the end-cap.

26. An end-cap assembly according to claim 25, wherein the end wall of the end-cap is substantially annular and the wall of the first chamber has a circular cross section decreasing from a first end of larger section, by which the first chamber is connected to the end wall of the end cap, to a second end of smaller cross section forming the passageway between the first chamber and the second chamber.

27. An end-cap assembly according to claim 24, wherein the degassing device has a longitudinal axis that is substantially parallel to and spaced apart from the central axis of the end wall of the end-cap, and
the end cap assembly further comprises:
a lateral nozzle for connecting an interior of the end-cap to an inlet of the first chamber of the degassing device.

28. An end-cap assembly according to claim 27, wherein the first chamber has a wall having a circular cross section increasing from a first end of smaller section, which forms the inlet of the first chamber, to a second end of larger cross section, which forms the passageway between the first and the second chambers.

29. A filtration device, comprising:
an elongated housing;
a filtration membrane arranged in the elongated housing; and
an end-cap assembly connected to the elongated housing, the end-cap assembly comprising:
an end-cap having:
an end wall having a central axis,
a peripheral wall surrounding the end wall for connection to an end of the housing, and
a degassing device according to claim 1 connected to the end-cap so that the first chamber of the degassing chamber is in fluid communication with an interior of the end-cap.

30. A filtration device according to claim 29, wherein the device is for extracorporeal treatment of blood.

31. A degassing device, comprising:
a first chamber having an inlet for a liquid; and
a second chamber having:
an upper opening closed by a hydrophobic membrane; and an outlet for discharging the liquid, wherein the outlet is at a higher elevation than the inlet of the first chamber, wherein the first chamber has a downstream portion that partially extends within the second chamber and communicates therewith by a passageway, the second chamber has a downstream portion that extends below the passageway and asymmetrically surrounds the downstream portion of the first chamber, wherein the outlet is in the downstream portion; the downstream portion has a lateral wall that surrounds a longitudinal axis of the first chamber and the downstream portion has a bottom wall that is inclined with respect to a longitudinal axis of the degassing device.

32. A degassing device, comprising:
a first chamber having an inlet for a liquid; and
a second chamber having:
    an upper opening closed by a hydrophobic membrane;
    an outlet for discharging the liquid, wherein the outlet is at a higher elevation than the inlet of the first chamber; and
    a wall delimiting the second chamber from the first chamber,
wherein the first chamber has a downstream portion that partially extends within the second chamber and communicates therewith by a passageway that opens in the second chamber close to an upper rim of the wall, the downstream portion of the first chamber is substantially frusto-conical, and the second chamber has a downstream portion that extends below the passageway and asymmetrically surrounds the downstream portion of the first chamber, and the outlet is in the downstream portion of the second chamber.

33. A degassing device, comprising:
a first chamber having an inlet for a blood liquid; and
a second chamber having;
    an opening closed by a hydrophobic membrane; and
    an outlet for discharging the blood liquid, at an elevation above the elevation of the first chamber;
wherein the first chamber has a downstream portion that partially extends within an upstream portion of the second chamber and communicates therewith by a passageway, the upstream portion of the second chamber extends above the passageway and has a decreasing cross-section, with a larger cross-section that is substantially level with the passageway and a smaller cross-section that is substantially level with the hydrophobic membrane, and the second chamber has a downstream portion which includes the outlet and that extends below the passageway and asymmetrically surrounds the downstream portion of the first chamber.

34. A degassing devices, comprising:
a first chamber having an inlet for a liquid; and
a second chamber having:
    an opening closed by a hydrophobic membrane; and
    an outlet for discharging the liquid, which is at a higher elevation than the inlet,
wherein the first chamber has a downstream portion that partially extends within the second chamber and communicates therewith by a passageway, and a ratio of a diameter of the passageway to a diameter of the second chamber at a level of the passageway is comprised between about 0.2 and about 0.5.

35. A degassing devices, comprising:
a first chamber having an inlet for a liquid; and
a second chamber having:
    an opening closed by a hydrophobic membrane; and
    a liquid inlet to receive another liquid to mix with the liquid in the second chamber;
    an outlet for discharging the liquid, at a higher elevation than the inlet to the first chamber;
wherein the first chamber has a downstream portion that partially extends within the second chamber and communicates therewith by a passageway, and the downstream portion of the first chamber has a cross-section selected with respect to a maximal flow rate of a liquid in a circuit connected to the degassing device so that a velocity of the liquid in the downstream portion of the first chamber is less than a predetermined velocity.

36. A degassing device, comprising:
a first chamber having an inlet for a liquid; and
a second chamber having:
    an opening closed by a hydrophobic membrane;
    a liquid inlet to receive another liquid to mix with the liquid in the second chamber, and
    an outlet for discharging the liquid, which is at a higher elevation than the inlet to the first chamber;
wherein the first chamber has a downstream portion that partially extends within the second chamber and communicates therewith by a passageway, and a cross-section of the second chamber of the degassing device at the level of the passageway is selected so that a ratio of a velocity of a liquid within a downstream portion of the first chamber to a velocity of the liquid within the second chamber at a level of the passageway is more than a determined value.

37. A degassing device, comprising:
a first chamber having an inlet for a liquid; and
a second chamber having:
    an opening closed by a hydrophobic membrane; and
    an outlet for discharging the liquid, which is at a higher elevation than the inlet of the first chamber;
wherein the first chamber has a downstream portion that partially extends within the second chamber and communicates therewith by a passageway, the second chamber has a downstream portion that extends below the passageway and asymmetrically surrounds the downstream portion of the first chamber, and the first chamber, the second chamber and the passageway therebetween are arranged with respect to each other so that a flow pattern of a liquid flowing from the first chamber, through the second chamber and to the outlet comprises a component that is tangential to the membrane.

38. A degassing device, comprising:
a first chamber having an inlet for a liquid; and
a second chamber having:
    an opening closed by a hydrophobic membrane; and
    an outlet for discharging the liquid, wherein the outlet is at a higher elevation than the inlet,
wherein the first chamber has a downstream portion that partially extends within the second chamber and communicates therewith by a passageway, and the first chamber, the second chamber and the passageway therebetween are arranged with respect to each other so that a flow of liquid flowing from the first chamber, through the second chamber and to the outlet port keeps gas bubbles in motion along an inner surface of the hydrophobic membrane.

39. A degassing device according to claim 32, wherein the upper rim of the wall is entirely in a plane substantially perpendicular to a longitudinal axis of the degassing device.

* * * * *